US00PP10916P

United States Patent [19]

VandenBerg

[11] Patent Number: Plant 10,916

[45] Date of Patent: May 25, 1999

[54] CHRYSANTHEMUM PLANT NAMED 'ESTRELLA'

[75] Inventor: Cornelis P. VandenBerg, Salinas, Calif.

[73] Assignee: Yoder Brothers, Inc., Barberton, Ohio

[21] Appl. No.: 08/990,908

[22] Filed: Dec. 15, 1997

[51] Int. Cl.[6] ..... A01H 5/00

[52] U.S. Cl. ..... Plt./78

[58] Field of Search ..... Plt./78

*Primary Examiner*—Howard J. Locker

*Attorney, Agent, or Firm*—C. A. Whealy

[57] ABSTRACT

A distinct cultivar of Chrysanthemum plant named 'Estrella', characterized by its large decorative spoon-type inflorescences that are about 8 cm in diameter; attractive bright yellow ray florets; numerous inflorescences per stem; numerous ray florets per inflorescence; large leaves; and exceptional postproduction longevity with inflorescences maintaining good substance and color for at least four weeks in an interior environment after one week of cool storage.

2 Drawing Sheets

The present invention relates to a new and distinct cultivar of Chrysanthemum plant, botanically known as *Dendranthema grandiflora* and referred to by the cultivar name Estrella.

The new cultivar is a product of a planned breeding program conducted by the inventor in Salinas, Calif. The objective of the breeding program is to create new cut Chrysanthemum cultivars having inflorescences with desirable colors and good form and substance.

The new cultivar originated from a cross made by the inventor in January, 1993, in Salinas, Calif., of the commercial cultivar Madera (disclosed in U.S. Plant Pat. No. 9,690) as the female, or seed, parent with an unnamed proprietary seedling selection, code number 3696, as the male, or pollen, parent. The female parent, the commercial cultivar Madera, is a bronze decorative spray-type cut Chrysanthemum. The male parent, seedling number 3696, is described as a bronze single spoon-type cut Chrysanthemum.

The cultivar Estrella was discovered and selected by the inventor as a flowering plant within the progeny of the stated cross in a controlled environment in Alva, Fla., in April, 1994. The selection of this plant was based on its desirable inflorescence color and good form and substance.

Asexual reproduction of the new cultivar by terminal cuttings taken in a controlled environment in Alva, Fla., has shown that the unique features of this new Chrysanthemum are stable and reproduced true to type in successive generations.

The cultivar Estrella has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Estrella'. These characteristics in combination distinguish 'Estrella' as a new and distinct cultivar:

1. Large decorative spoon-type inflorescences that are about 8 cm in diameter.
2. Attractive bright yellow ray florets.
3. Numerous inflorescences per stem.
4. Numerous ray florets per inflorescence.
5. Large leaves.
6. Exceptional postproduction longevity with inflorescences maintaining good substance and color for at least four weeks in an interior environment after one week of cool storage.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the first sheet comprises a side perspective view of a typical flowering stem of 'Estrella' grown as a spray-type cut Chrysanthemum.

The photograph at the bottom of the first sheet comprises a side perspective view of typical inflorescences of the cultivar Estrella.

The photograph at the top of the second sheet comprises a top perspective view of upper (left) and lower (right) surfaces of typical inflorescences of the cultivar Estrella.

The photograph at the bottom of the second sheet comprises a top perspective view of the upper (left) and lower (right) surfaces of leaves of the cultivar Estrella. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under commercial practice in a polyethylene-covered greenhouse. Rooted cuttings were planted Apr. 25, 1997 and cut flowers were harvested on Jul. 10, 1997. After planting rooted cuttings of the new cultivar, plants received 18 long day/short nights following by short day/long nights until flowering. Measurements and numerical values represent averages for five typical flowering stems.

Botanical classification: *Dendranthema grandiflora* cultivar Estrella.

Commercial classification: Decorative spray-type cut Chrysanthemum.

Parentage:

*Male or pollen parent.*—Unnamed proprietary *Dendranthema grandiflora* seedling selection, code number 3696.

*Female or seed parent.*—*Dendrantheam grandiflora* cultivar Madera (disclosed in U.S. Plant Pat. No. 9,690).

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative spray-type cut flower. Stems upright, uniform habit and freely branching.

*Flowering stem length.*—About 81 cm.

*Stem color.*—147B.

*Foliage description.*—Arrangement: Alternate. Length: About 14 cm. Width: About 11 cm. Apex: Acuminate to aristate. Base: Attenuate. Margin: Palmately lobed. Texture: Abaxial and lower surfaces slightly pubescent. Veins prominent on lower surface. Color: Young foliage upper surface: 147A. Young foliage lower surface: Between 147A and 147B. Mature foliage upper surface: 147A. Mature foliage lower surface: 147B. Venation upper surface: 147B. Venation lower surface: 147B. Petiole: Length: About 3 cm. Color: 147B/147C.

Flowering description:

*Appearance.*—Decorative spray-type inflorescence form with spoon-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two to three weeks of long day/short night conditions after planting followed by photoinductive short day/long night conditions flower about 58 days later.

*Postproduction longevity.*—In an interior environment, flowering stems will maintain good color and substance for at least four weeks in an interior environment after one week of cool storage.

*Quantity of inflorescences.*—About 14 inflorescences per flowering stem.

*Inflorescence size.*—Diameter: About 8 cm. Depth (height): About 2.5 cm. Diameter of disc: About 3 mm.

*Ray florets.*—Shape: Flattened tube with open spoon. Length: About 4 cm. Tube length: About 2.5 cm. Width: About 7.5 mm. Apex: Rounded. Base: Tubular. Margin: Entire. Texture: Satiny, smooth, glabrous. Aspect: Recurved. Number of ray florets per inflorescence: About 210. Color: When opening: 5A. Mature: Upper surface: 5A. Lower surface: 5A.

*Disc florets.*—Shape: Tubular. Length: About 5 mm. Width: About 1 mm. Color: Immature: 154A. Mature: Apex: 13A/15A. Base: White.

*Peduncle.*—Aspect: Strong and angled about 30° to the stem. Length: First peduncle: About 12 cm. Fourth peduncle: About 15 cm. Seventh peduncle: About 18.5 cm. Texture: Very fine pubescence. Color: 147B.

*Reproductive organs.*—Androecium: Present on disc florets only. Anther color: 14A. Pollen: Moderate, 14A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Estrella', as illustrated and described.

* * * * *

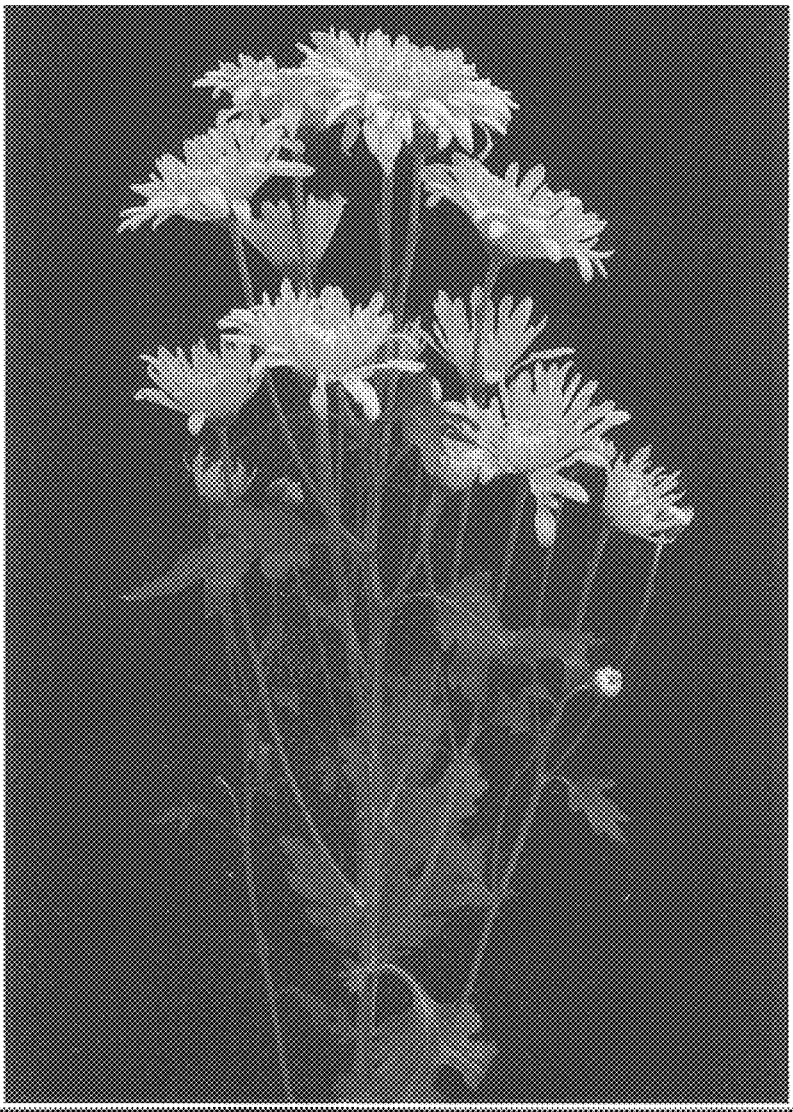
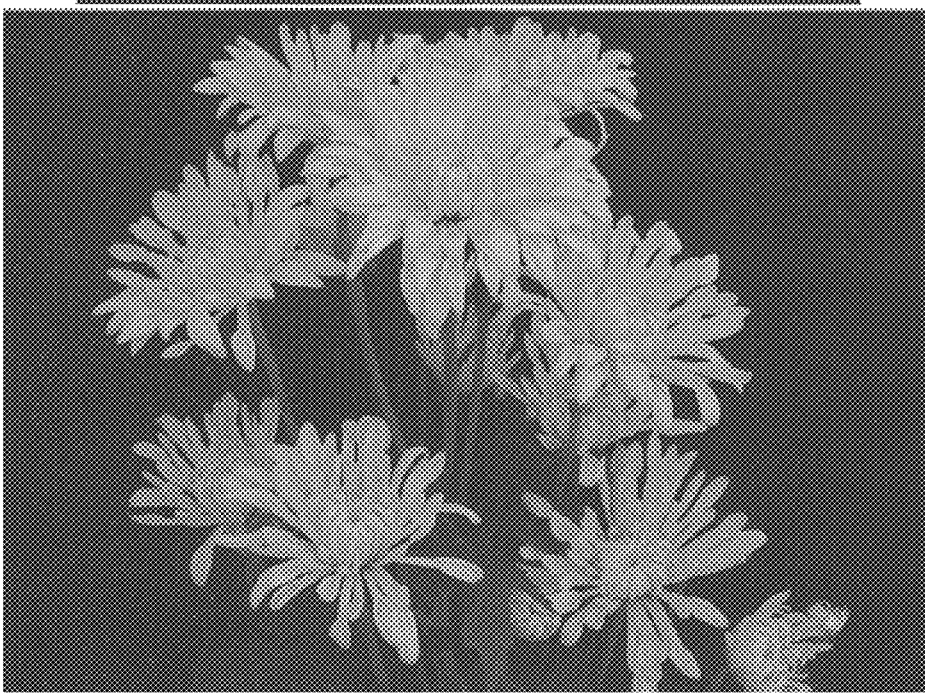

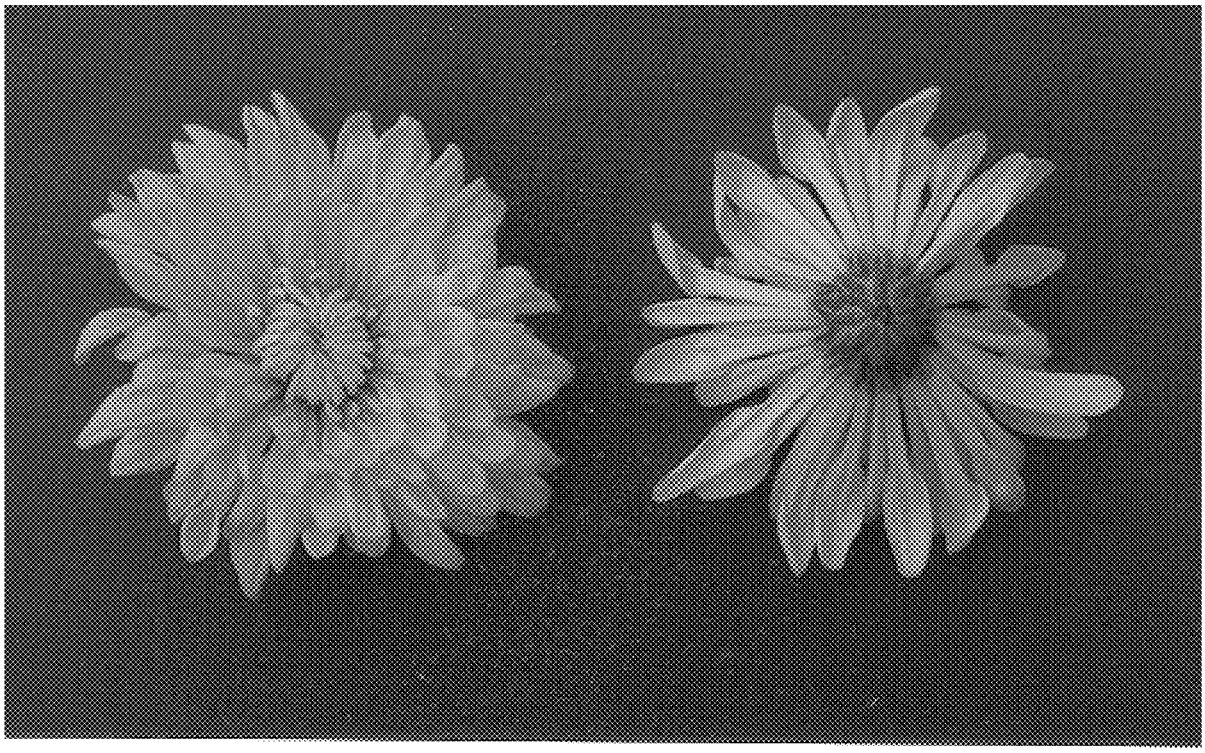
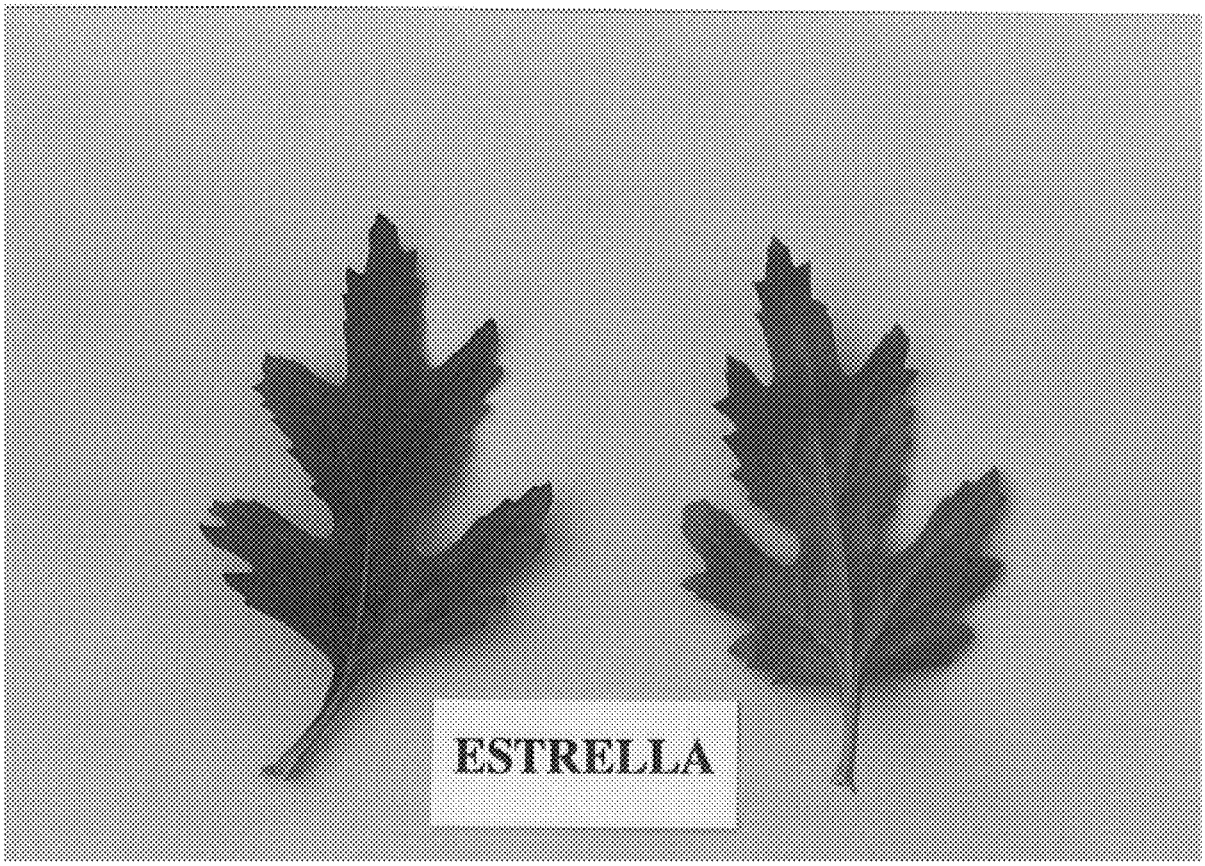
ESTRELLA